（12） United States Patent
Albert

(10) Patent No.: US 9,986,925 B2
(45) Date of Patent: Jun. 5, 2018

(54) TWO ELECTRODE APPARATUS AND METHODS FOR TWELVE LEAD ECG

(71) Applicant: AliveCor, Inc., Mountain View, CA (US)

(72) Inventor: David E. Albert, Mountain View, CA (US)

(73) Assignee: ALIVECOR, INC., Mountain View, CA (US)

( * ) Notice: Subject to any disclaimer, the term of this patent is extended or adjusted under 35 U.S.C. 154(b) by 0 days. days.

(21) Appl. No.: 15/721,038

(22) Filed: Sep. 29, 2017

(65) Prior Publication Data

US 2018/0020939 A1 Jan. 25, 2018

Related U.S. Application Data

(63) Continuation of application No. 15/140,072, filed on Apr. 27, 2016, now Pat. No. 9,833,158, which is a continuation of application No. 14/254,310, filed on Apr. 16, 2014, now Pat. No. 9,351,654, said application No. 15/140,072 is a continuation-in-part of application No. 13/108,738, filed on May 16, 2011, now abandoned, which is a continuation-in-part of application No. 12/796,188, filed on Jun. 8, 2010, now Pat. No. 8,509,882.

(60) Provisional application No. 61/812,655, filed on Apr. 16, 2013.

(51) Int. Cl.
*A61B 5/00* (2006.01)
*A61B 5/04* (2006.01)
*G06Q 50/22* (2018.01)
*A61B 5/0432* (2006.01)
*A61B 5/0402* (2006.01)
*A61B 5/044* (2006.01)
*A61B 5/0408* (2006.01)
*A61B 5/0404* (2006.01)
*A61B 5/0245* (2006.01)
*A61B 5/0452* (2006.01)
*A61B 5/0205* (2006.01)

(52) U.S. Cl.
CPC .......... *A61B 5/04012* (2013.01); *A61B 5/002* (2013.01); *A61B 5/0006* (2013.01); *A61B 5/0015* (2013.01); *A61B 5/0022* (2013.01); *A61B 5/0245* (2013.01); *A61B 5/0404* (2013.01); *A61B 5/044* (2013.01); *A61B 5/0408* (2013.01); *A61B 5/04028* (2013.01); *A61B 5/0432* (2013.01); *A61B 5/0452* (2013.01); *A61B 5/6898* (2013.01); *G06Q 50/22* (2013.01); *A61B 5/0205* (2013.01)

(58) Field of Classification Search
CPC ........................... A61B 5/0404; A61B 5/0006
USPC ........................................ 600/323, 309, 509
See application file for complete search history.

*Primary Examiner* — Nadia A Mahmood
(74) *Attorney, Agent, or Firm* — Womble Bond Dickinson (US) LLP; Christopher Kokoska

(57) ABSTRACT

Described herein are methods, apparatuses, and systems for heart monitoring of a patient. The heart monitoring system can be used to take an electrocardiogram (ECG) using only two electrodes. A handheld device can be used to sequentially measure the electrical signal between different positions on a patient's body. The electrical signals can be processed and analyzed to prepare an ECG for the patient, including a 12-lead ECG.

36 Claims, 10 Drawing Sheets

TWO ELECTRODE APPARATUS AND METHODS FOR TWELVE LEAD ECG

CROSS REFERENCE TO RELATED APPLICATIONS/INCORPORATION BY REFERENCE STATEMENT

This application is a continuation of U.S. patent application Ser. No. 15/140,072, filed Apr. 27, 2016, which is a continuation of U.S. patent application Ser. No. 14/254,310, filed Apr. 16, 2014, now U.S. Pat. No. 9,351,654, issued on May 31, 2016; which is a continuation-in-part of U.S. Ser. No. 13/108,738, filed May 16, 2011, which is a continuation-in-part of U.S. Ser. No 12/796,188, filed Jun. 8, 2010, now U.S. Pat. No. 8,509,882, issued Aug. 13, 2013, each of which is hereby expressly incorporated herein by reference in its entirety. U.S. patent application Ser. No. 14/254,310 also claims priority to U.S. Provisional Application No. 61/812,655, filed on Apr. 16, 2013 which is hereby expressly incorporated herein by reference in its entirety.

BACKGROUND OF THE INVENTIVE CONCEPTS

1. Field of the Inventive Concepts

The presently claimed and disclosed inventive concept(s) relates generally to heart monitoring devices and methods and, more particularly, but not by way of limitation, to devices, systems and software for generating and providing one or more 12-lead electrocardiograms utilizing only two electrodes.

2. Brief Description of Related Art

Electrocardiography has been used to study the electrical activity of the heart. Electrocardiograms (ECG) can be recorded or taken using electrodes placed on the skin of a patient. The electrical signals recorded between any two electrodes placed on the skin of the patient are referred to as "leads." Varying numbers of electrodes and leads can be used to take the ECG. Exemplary numbers of leads used conventionally for taking ECGs are 3, 5, and 12 leads. For a standard 12-lead ECG, ten electrodes are used with six electrodes positioned on the chest and one electrode on each of the patient's arms and legs.

FIG. 1 is a pictorial representation of the 10 electrodes of a conventional electrocardiograph being placed on the patient for obtaining a standard 12-lead ECG. The electrode placed on the right arm is commonly referred to as RA. The electrode placed on the left arm is referred to as LA. The RA and LA electrodes are placed at the same location on the left and right arms, preferably but not necessarily near the wrist. The leg electrodes can be referred to as RL for the right leg and LL for the left leg. The RL and LL electrodes are placed on the same location for the left and right legs, preferably but not necessarily near the ankle.

FIG. 2 illustrates the placement of the six electrodes on the chest in the prior art arrangement with such electrodes being labeled $V_1$, $V_2$, $V_3$, $V_4$, $V_5$, and $V_6$. $V_1$ is placed in the fourth intercostal space, for example between ribs 4 and 5, just to the right of the sternum. $V_2$ is placed in the fourth intercostal space, for example between ribs 4 and 5, just to the left of the sternum. $V_3$ is placed in the fifth intercostal space midway between electrodes $V_2$ and $V_4$. $V_4$ is placed in the fifth intercostal space between ribs 5 and 6 on the left mid-clavicular line. $V_5$ is placed horizontally even with $V_4$ on the left anterior axillary line. $V_6$ is placed horizontally even with $V_4$ and $V_5$ on the left mid-axillary line.

The electrocardiograph then calculates and outputs three limb lead waveforms. Limb leads I, II, and III are bipolar leads having one positive and one negative pole. Lead I is the voltage between the left arm (LA) and right arm (RA), e.g. I=LA−RA. Lead II is the voltage between the left leg (LL) and right arm (RA), e.g. II=LL−RA. Lead III is the voltage between the left leg (LL) and left arm (LA), e.g. III=LL−LA. Leads I, II and III are commonly referred to as "limb leads."

Unipolar leads also have two poles; however, the negative pole is a composite pole made up of signals from multiple other electrodes. In a conventional cardiograph for obtaining a 12-lead ECG, all leads except the limb leads are unipolar (aVR, aVL, aVF, $V_1$, $V_2$, $V_3$, $V_4$, $V_5$, and $V_6$). Augmented limb leads (aVR, aVL, and aVF) view the heart from different angles (or vectors) and are determined from RA, RL, LL, and LA. For example, the augmented vector right (aVR) positions the positive electrode on the right arm, while the negative electrode is a combination of the left arm electrode and the left leg electrode, which "augments" the signal strength of the positive electrode on the right arm. Thus the augmented vector right (aVR) is equal to RA−(LA+LL)/2 or −(I+II)/2. The augmented vector left (aVL) is equal to LA−(RA+LL)/2 or (I−II)/2. The augmented vector foot (aVF) is equal to LL−(RA+LA)/2 or (II−I)/2.

The six electrodes on the chest of the patient are close enough to the heart that they do not require augmentation. A composite pole called Wilson's central terminal (often symbolized as $CT_W$, $V_W$, or WCT) is used as the negative terminal. Wilson's central terminal is produced by connecting the electrodes RA, LA, and LL together, via a simple resistive network, to give an average potential across the body, which approximates the potential at an infinite distance (i.e. zero). Wilson's central terminal, WCT, is calculated as (RA+LA+LL)/3.

FIG. 3 illustrates an example Lead I annotated to show PQRST waves generated by a 12-lead electrocardiograph. The identification and measurement of the PQRST waves based on the electrocardiogram is known in the art. FIG. 4 illustrates an example of a 12-lead electrocardiogram in a conventional format.

While a conventional 12-lead electrocardiogram gives very useful information concerning the health and condition of an individual's heart, the conventional electrocardiograph equipment is expensive and the procedure is not normally available in areas other than hospitals and medical doctors' offices. Therefore monitoring is not done frequently even in wealthy countries, and in poorer areas of the world an electrocardiograph may not even be available. To significantly reduce costs of obtaining an electrocardiogram, a 2-electrode electrocardiograph device as described in U.S. Pat. No. 8,301,232 was marketed. The 2-electrode electrocardiograph device utilizes a smart phone connected to and at least partially surrounded by a phone protective case incorporating and supporting the two electrodes. Such devices significantly simplify and reduce the cost of obtaining an electrocardiogram, although such an electrocardiogram does not include as much information as a 12-lead electrocardiogram produced by an electrocardiograph having 10 electrodes. The 12-lead electrocardiogram produced by the 10-electrode electrocardiograph offers additional and important heart-related information to the cardiologist, allowing the diagnosis of conditions like heart attacks (myocardial infarctions) that a single-lead ECG cannot do. It would be advantageous if a readily available and inexpensive device could generate and produce an electrocardiogram that substantially replicates the 12-lead electrocardiogram produced by a 10-electrode electrocardiograph.

SUMMARY OF THE DISCLOSURE

In general, described herein are apparatuses, methods and systems for producing an electrocardiogram that substantially replicates the electrocardiogram produced by a 10-electrode electrocardiograph but using an electrocardiograph device having only two electrodes. In one embodiment, the electrocardiograph device has a first electrode assembly with a first electrode adapted to measure an electrical signal on a patient's body, and a second electrode assembly with a second electrode adapted to measure an electrical signal at another location on the patient's body. The electrocardiograph device also includes control circuitry configured to measure electrocardiogram signals between the first and second electrodes, and a data transmission module configured to transmit the measured electrocardiogram signals to a portable computing device by a wired or wireless transmission system and protocol such as, for example, those known in the art as USB, WI-FI®, BLUETOOTH®, NFC, or as audible or ultrasonic sound signals.

The electrocardiograph device can be used in combination with a portable computing device to form an electrocardiograph. The portable computing device is provided with computer hardware including a processor in communication with a non-transitory computer readable medium. The non-transitory computer readable medium stores software that includes instructions that when executed by the processor causes the processor to record the electrocardiogram signals between the first electrode and the second electrode while the first and second electrodes are sequentially placed in predetermined paired positions on a patient's body that are known by the processor. In one embodiment the processor is caused to (a) calculate an average PQRST beat from the measured electrocardiogram signals as the first and second electrodes are sequentially placed in Limb Lead I, II, and III positions on a patient's body for a time required to measure at least one heartbeat in each Limb Lead position, the Limb Lead positions known by the processor; (b) use the relationship (Lead III=Lead II−Lead I) to time-align and display Limb Leads I, II, and III; and (c) calculate and display augmented Leads aVR, aVL, and aVF from the time-aligned Limb Leads I, II, and III.

The software can further include instructions that when executed by the processor causes the processor to calculate and display average time-aligned Leads V1, V2, and V3 from the measured electrocardiogram signals obtained from sequentially placing one of the first and second electrodes in a V1, V2, and V3 position while contacting the other of the first and second electrodes with a left arm of the patient for a time required to measure at least one heart beat (or more if an average beat is to be calculated). The processor is further caused to calculate and display average Leads V4, V5, and V6 from the measured electrocardiogram signals obtained from sequentially placing one of the first and second electrodes in a V4, V5, and V6 position while contacting the other of the first and second electrodes with a right arm of the patient for a time required to measure at least one heartbeat. The resulting 12-lead display and report replicated the 12-lead electrocardiogram produced by a 10-electrode electrocardiograph.

Methods are provided for generating a 12-lead electrocardiogram using an electrocardiograph comprising an electrocardiograph device and a portable computing device. The electrocardiograph device has a first electrode, a second electrode, control circuitry, and a data transmission module, the control circuitry configured to measure electrocardiogram signals between the first and second electrodes. In one embodiment, such a method includes directing, by the portable computing device, a user to place the first electrode and the second electrode at predetermined locations on a patient's body. The portable computing device receives and records location data indicative of the predetermined location on which the first electrode and the second electrode are placed. The control circuitry of the electrocardiograph device receives electrocardiogram signals from the first electrode and the second electrode, and the data transmission module of the electrocardiograph device transmits the electrocardiogram signals to the portable computing device. The portable computing device generates a 12-lead electrocardiogram from the sequentially measured electrocardiogram signals between the first and second electrodes.

DETAILED DESCRIPTION

Figure 1:
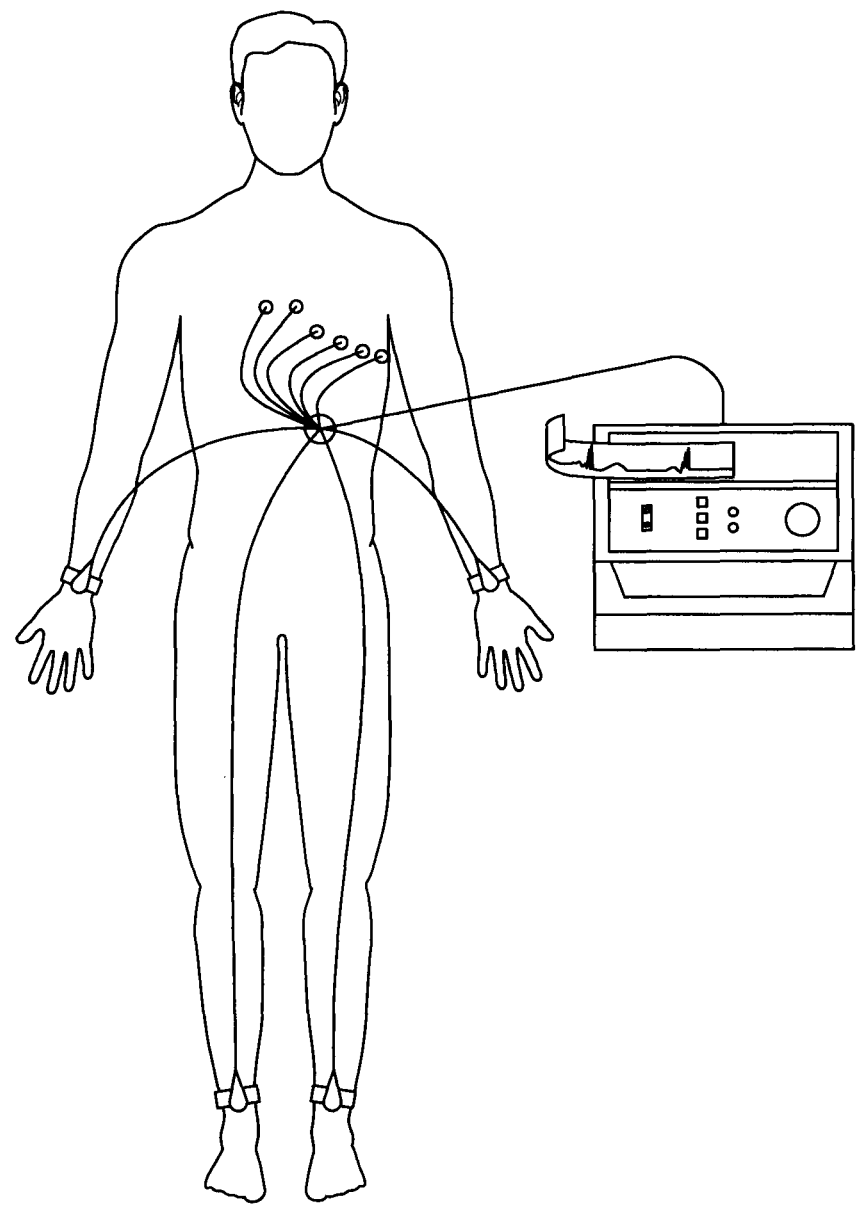
FIG. 1 is a pictorial representation of a prior art electrocardiograph having 10 electrodes positioned on a patient's body for taking a prior art 12-lead electrocardiogram.
Figure 2:
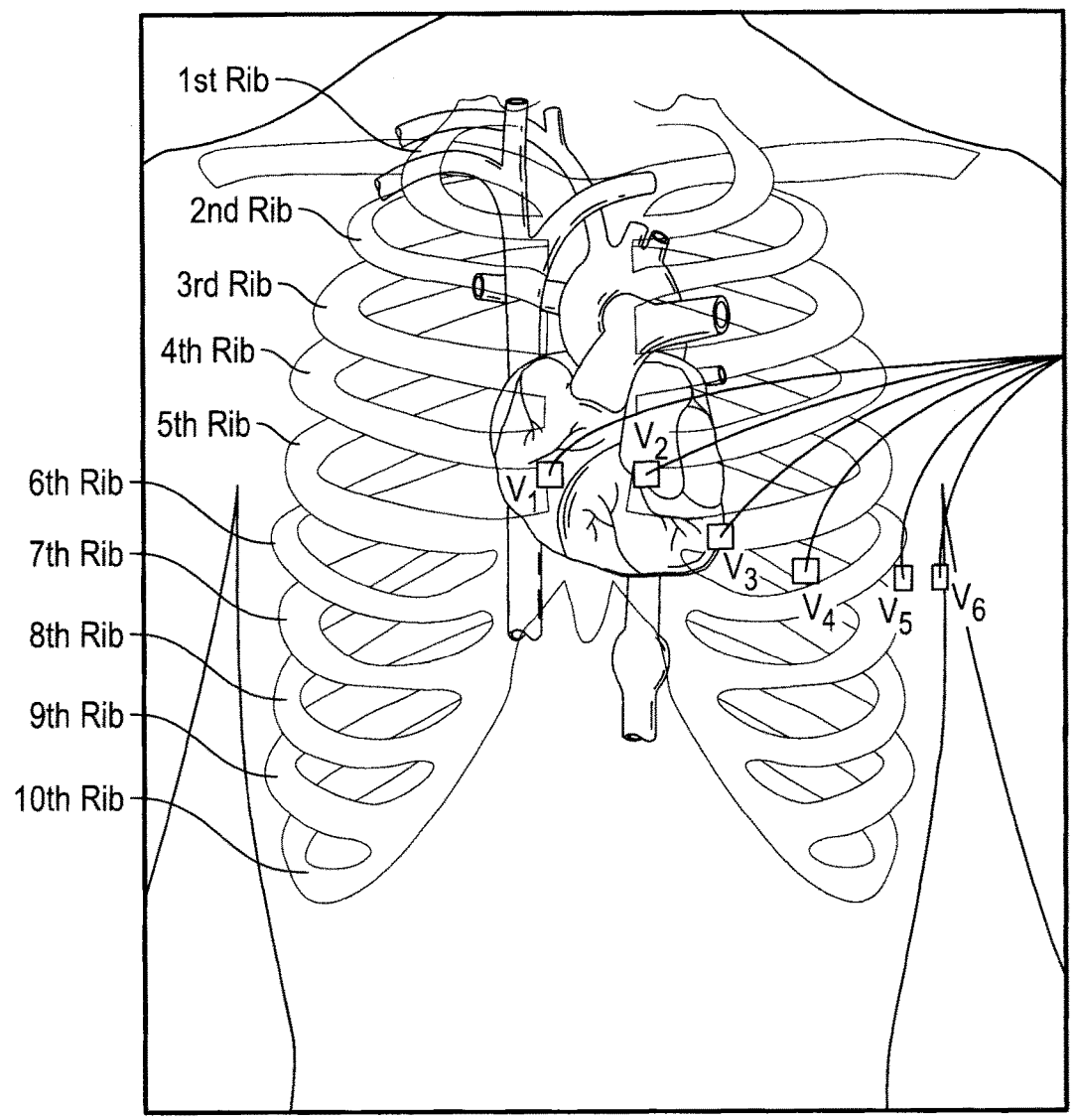
FIG. 2 is a pictorial representation of a chest showing an example of electrode placement on the chest for taking a prior art 12-lead electrocardiogram.
Figure 3:
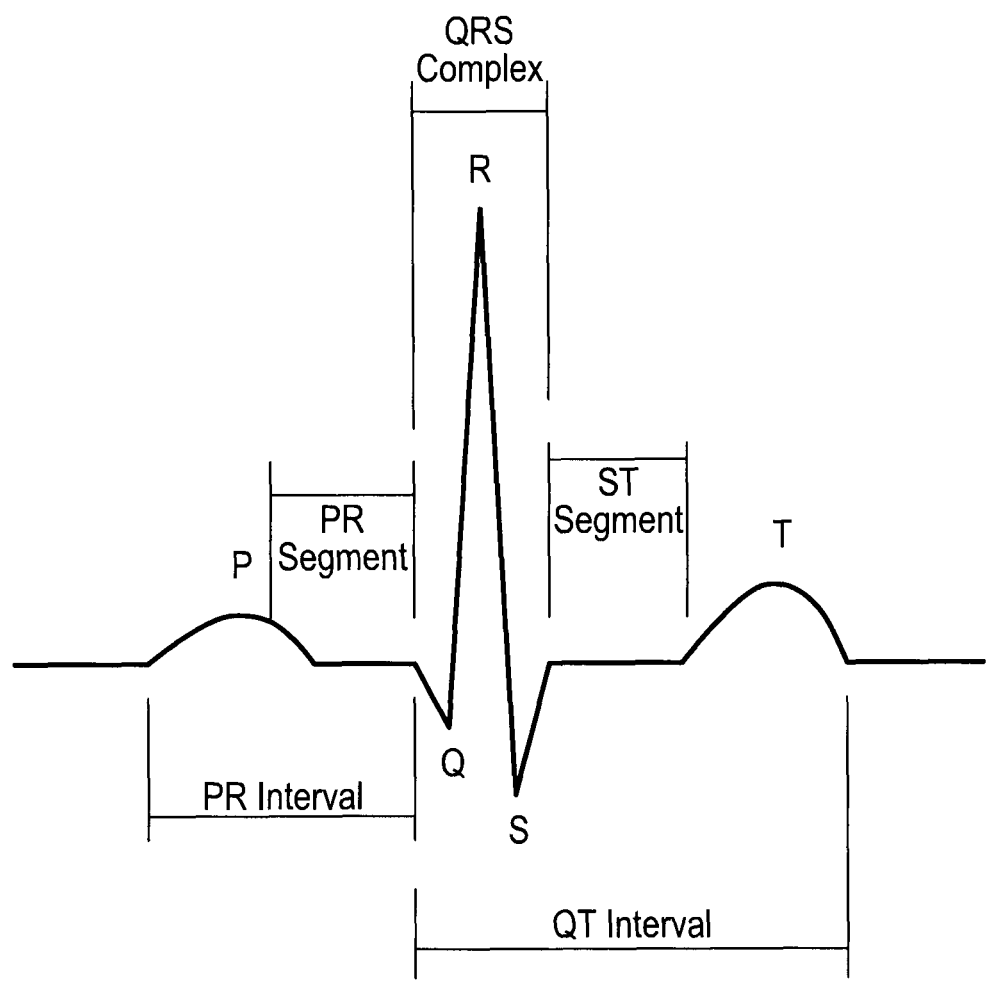
FIG. 3 illustrates an example Lead I annotated to show PQRST waves generated by a 12-lead electrocardiograph.

Before explaining at least one embodiment of the inventive concepts disclosed herein in detail, it is to be understood that the inventive concepts are not limited in their application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for purpose of description only and should not be regarded as limiting in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Figure 4:
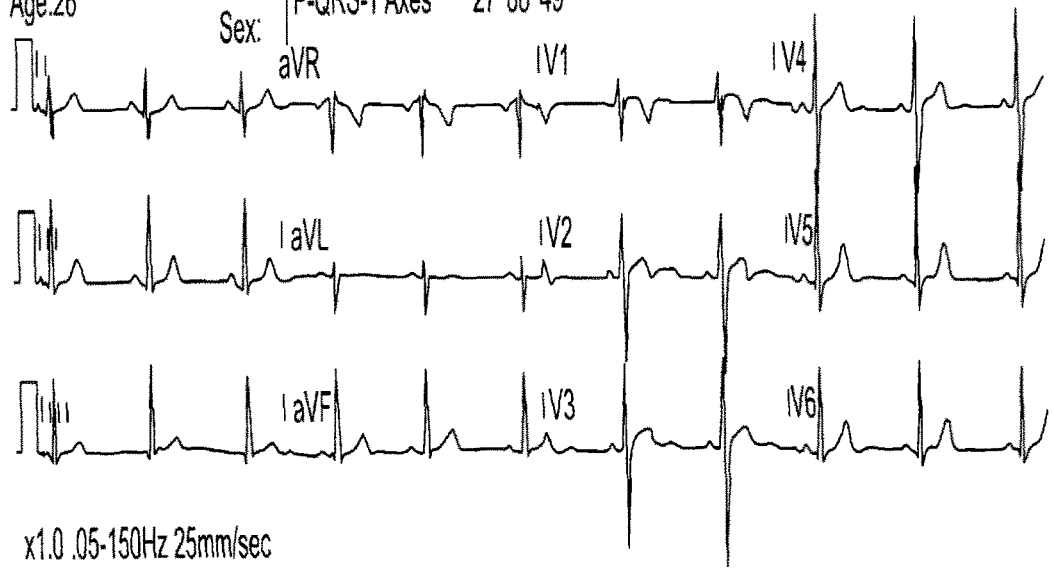
FIG. 4 shows an example 12-lead electrocardiogram in a conventional format.

The term "lead" in electrocardiography causes much confusion because it can be used to refer to two different things. In accordance with common usage, the word "lead" may be used to refer to the electrical cable attaching the electrodes to the electrocardiograph. Alternatively, and as used herein, the word "lead" refers to the tracing of the voltage difference between at least two electrodes. Conventionally, 10 electrodes are used to produce twelve of this type of lead, thereby forming a "12-lead" electrocardiogram as exemplified in FIG. 4.

A "12-lead electrocardiogram format" is used herein and in the appending claims to refer to presentation of electrocardiogram signals from at least Lead I, Lead II, and $V_1$ through $V_6$ leads, and optionally Lead III, aVR, aVL and aVF, displayed over the span of at least one heartbeat using a uniform time scale.

The term "patient" as used herein includes humans and other warm-blooded animals, such as mammals, for example, dogs, cats, horses, and cattle or cold-blooded animals such as reptiles, and refers to the person or animal whose heart-related signals are being measured. The term "user" refers to the one applying the electrodes to the body to measure the ECG. The user can be the same as the patient, or the user can be another such as, for example, a nurse, doctor, or veterinarian.

Figure 5A:
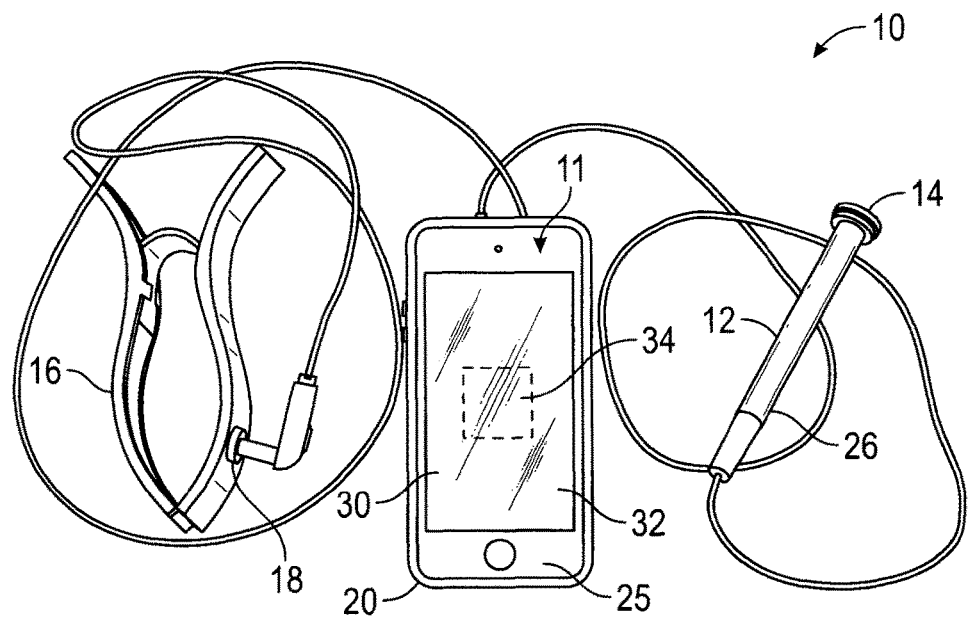
FIG. 5A illustrates a front elevational view of one embodiment of an electrocardiograph constructed in accordance with the presently disclosed and claimed inventive concepts in which the electrocardiograph includes a two-electrode electrocardiograph device and a portable computing device.
Figure 5B:
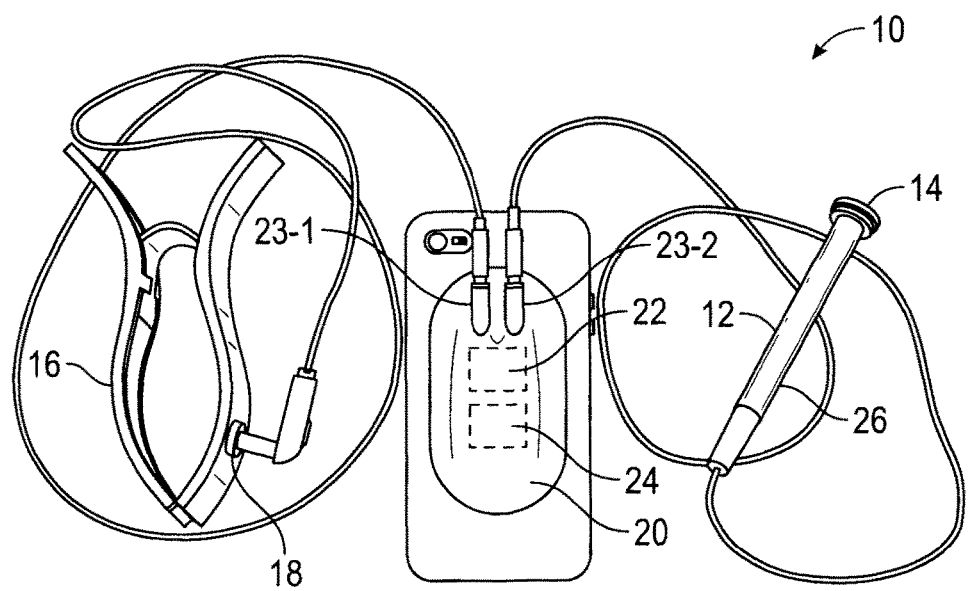
FIG. 5B illustrates a rear elevational view of the electrocardiograph depicted in FIG. 5A.

In general methods, devices, and systems are provided for measuring electrical signals on the body of a patient. Referring now to FIGS. 5A and 5B, shown therein is an exemplary embodiment of an electrocardiograph 8 constructed in accordance with the inventive concepts disclosed and claimed herein. The electrocardiograph 8 includes an electrocardiograph device 10 and a portable computing device 11. The electrocardiograph device 10 as discussed below is a two-electrode device; however, it should be understood that the electrocardiograph device 10 may include more than two electrodes. The electrocardiograph device 10 includes a first electrode assembly 12 having a first electrode 14, a second electrode assembly 16 having a second electrode 18, and a housing 20 containing control circuitry 22 and a data transmission module 24. The first electrode 14 and the second electrode 18 are adapted to measure an electrical signal on a patient's body. The control circuitry 22, can communicate with the first and second electrodes 14 and 18 via ports 23-1 and 23-2, respectively, and is configured to measure electrocardiogram signals between the first and second electrodes 14 and 18, respectively. The electrocardiogram signals can be analog signals indicative of the electrical potentials on a body surface of the patient that are associated with heart muscle activity. The ports 23-1 and 23-2 may be designed to receive analog signals, and may include two, three or four contacts. In some embodiments, the ports 23-1 and 23-2 are standard female connectors in which a three-contact version is known in the art as a TRS connector, where T stands for "tip", R stands for "ring" and S stands for "sleeve". Similarly, two- and four-contact versions are known in the art as TS and TRRS connectors respectively.

The data transmission module 24 is configured to receive the measured electrocardiogram signals and transmit the measured electrocardiogram signals to the portable computing device 11. The data transmission module 24 may transmit the measured electrocardiogram signals to the portable computing device 11 using a wired or wireless transmission system and protocol such as those known in the art as USB, WI-FI®, BLUETOOTH®, NFC, or as audible or ultrasonic sound signals.

While there can be multiple electrodes, in one embodiment there are only two. The first electrode assembly 12 can be configured in any way consistent with its function, i.e., it should include the first electrode 14 in a manner available to make contact with a patient's body on the hands, chest or other parts of the body, to measure an electrical signal for obtaining the patient's electrocardiogram. The first electrode assembly 12 can include a non-conductive hand-held portion 26 as well as the first electrode 14. By using only two electrodes, and sequentially measuring electrocardiogram signals at separate and distinct instants of time as discussed below, a patient can easily measure his or her own electrocardiogram signals and produce a 12-lead electrocardiogram without the need to apply 10 electrodes and adhesives to the body as would be the case using a conventional electrocardiograph.

The second electrode assembly 16 can likewise be configured in any way consistent with its function. In one embodiment, the second electrode assembly 16 is configured to removably attach to an upper limb of the patient. For example, the electrocardiograph device 10 shown in FIGS. 5A and 5B includes a second electrode assembly 16 configured as a spring-hinged cuff. By allowing the second electrode assembly 16 to "grasp" the patient rather than the patient grasping an electrode, little or no electrical "noise" is created by the nerves and adjacent muscles holding the second electrode 18.

Other nonlimiting examples of suitable electrodes include suction cup electrodes, disposable snap electrodes, alligator clip electrode connectors with disposable electrodes, and any combination thereof.

The portable computing device 11 can be implemented as a personal computer, a smart phone, network-capable TV set, TV set-top box, a tablet, an e-book reader, a laptop computer, a desktop computer, a network-capable handheld device, a video game console, a server, and combinations thereof, for example. Preferably, the portable computing device 11 comprises an input device 30, an output device 32, and computer hardware 34 (which is shown in Phantom). The computer hardware 34 may be a system or systems that are able to embody and/or execute the logic of the processes described herein. Logic embodied in the form of software instructions and/or firmware may be executed on any appropriate hardware. For example, logic embodied in the form of software instructions or firmware may be executed on a dedicated system or systems, or on a personal computer system, or on a distributed processing computer system, and/or the like. In some embodiments, logic may be implemented in a stand-alone environment operating on a single computer system and/or logic may be implemented in a networked environment, such as a distributed system using multiple computers and/or processors. The computer hardware 34 of the portable computing device 11 may have a processor and a non-transitory computer readable medium. The term "processor" as used herein may include a single processor or multiple processors working independently and/or together to execute the logic described herein. Exemplary non-transitory computer readable medium may include random access memory, read only memory, flash memory, and combinations thereof. The term non-transitory computer readable medium, as used herein, may be implemented as a single physical device or multiple physical devices of a distributed system that may or may not be logically related.

The input device 30 is capable of receiving information input from a user, and transmitting such information to the computer hardware 34. The input device 30 can be implemented as a keyboard, a touchscreen, a mouse, a trackball, a microphone, a fingerprint reader, an infrared port, a slide-out keyboard, a flip-out keyboard, a cell phone, a PDA, a video game controller, a remote control, a fax machine, and combinations thereof, for example.

The output device 32 outputs information in a form perceivable by a user. For example, the output device 32 can be a computer monitor, a screen, a touchscreen, a speaker, a website, a TV set, a smart phone, a PDA, a cell phone, a fax machine, a printer, a laptop computer, and combinations thereof. It is to be understood that the input device 30 and the output device 32 may be implemented as a single device, such as for example a touchscreen of a smartphone or a tablet.

Figure 5C:
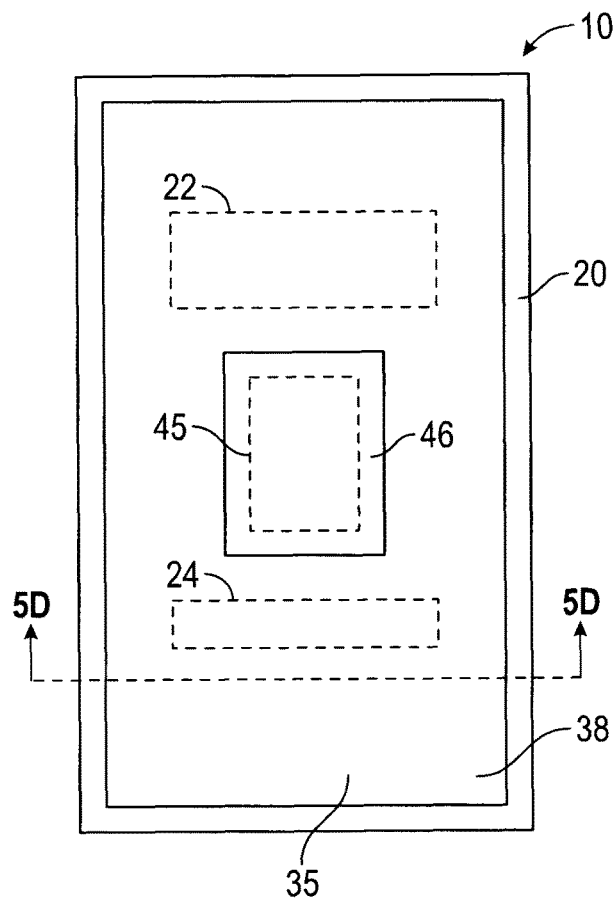
FIG. 5C is a front elevational view of the electrocardiograph device depicted in FIG. 5A in which the electrocardiograph device has been removed from the portable computing device.
Figure 5D:
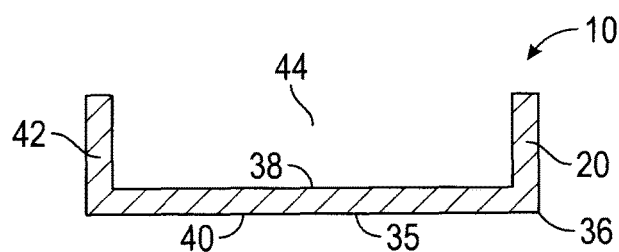
FIG. 5D is a cross-sectional view of the electrocardiograph device depicted in FIG. 5C and taken along the lines 5-5.

In one embodiment, the housing 20 is configured as a protective cover for the portable computing device 11. As shown in FIG. 5C and FIG. 5D, the housing 20 may be provided with a base 35 having a perimeter 36. The base 35 has an interior surface 38 and an opposing exterior surface 40. The housing 20 may also be provided with a rim 42 extending from the interior surface 38 and generally following the perimeter 36 of the base 35. The rim 42 and the interior surface 38 define a space 44 that is sized and adapted to receive the portable computing device 11. The ports 23A and 23B may be proximate to the exterior surface 40 so as to be available when the portable computing device 11 is positioned within the space 44. The base 35, in some embodiments, surrounds and supports the control circuitry 22 and the data transmission module 24. In this embodiment, the base 35 may include a pocket for receiving a power source 45, such as a battery, for powering the control circuitry 22 and the data transmission module 24 and may also include a door 46 proximate to the interior surface 38 for providing access to the pocket such that a user can install and/or replace the power source 45. In other embodiments, the power source 45 maybe a solar cell supported by the base 35 proximate to the exterior surface 40.

The housing 20 may be constructed as a single unit, or multiple units connected together. Exemplary materials forming the housing 20 include plastic, and/or a combination of plastic and elastomers.

Figure 6:
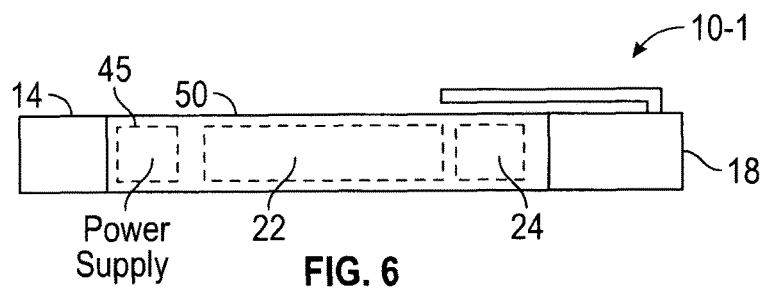
FIG. 6 an other embodiment of a two-electrode electrocardiograph device configured in a pen-shape and constructed in accordance with the inventive concepts disclosed herein.
Figure 7C:
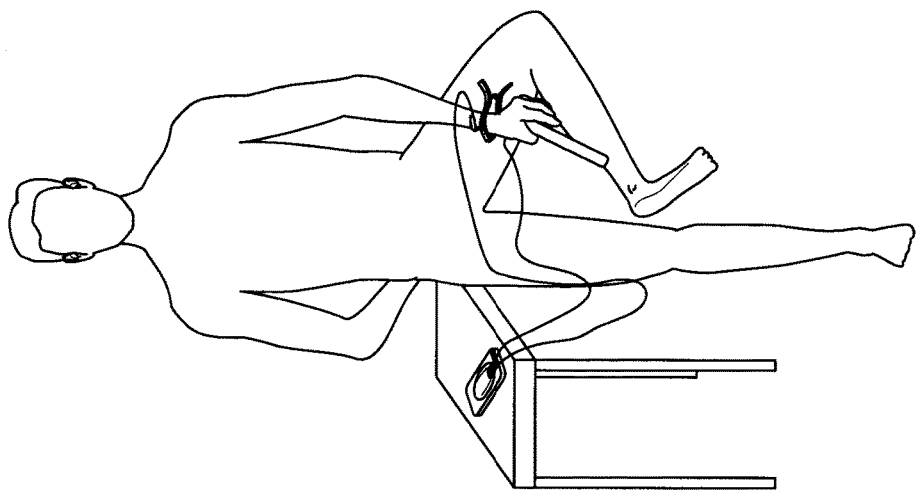
FIG. 7A-FIG. 7E illustrates an example sequential electrode placement used by the electrocardiograph to generate a 12-lead electrocardiogram in accordance with the presently disclosed inventive concepts.
Figure 7B:
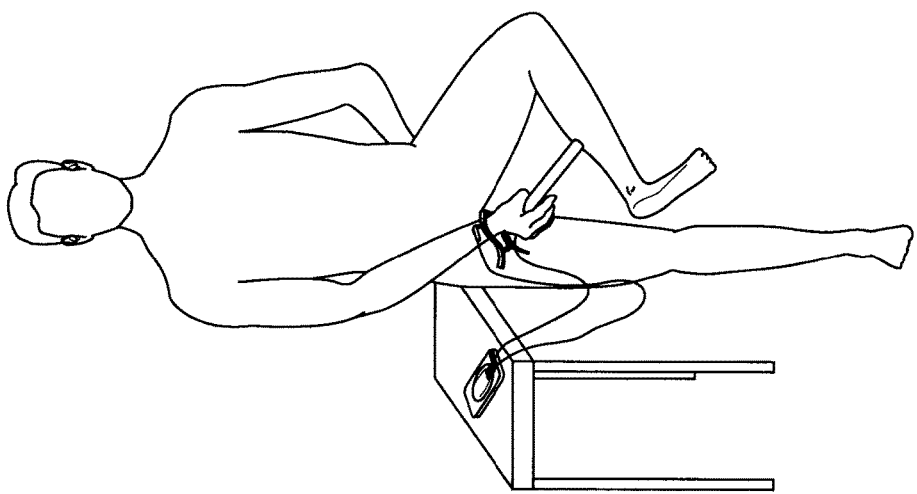
Figure 7A:
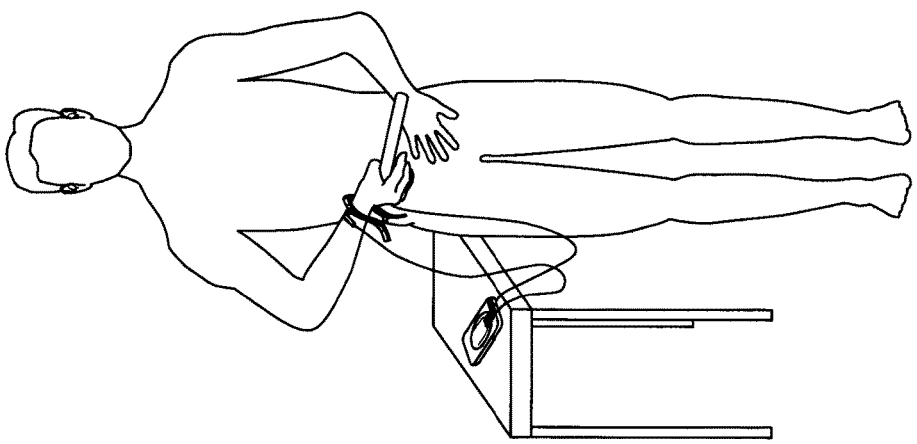
Figure 7D:
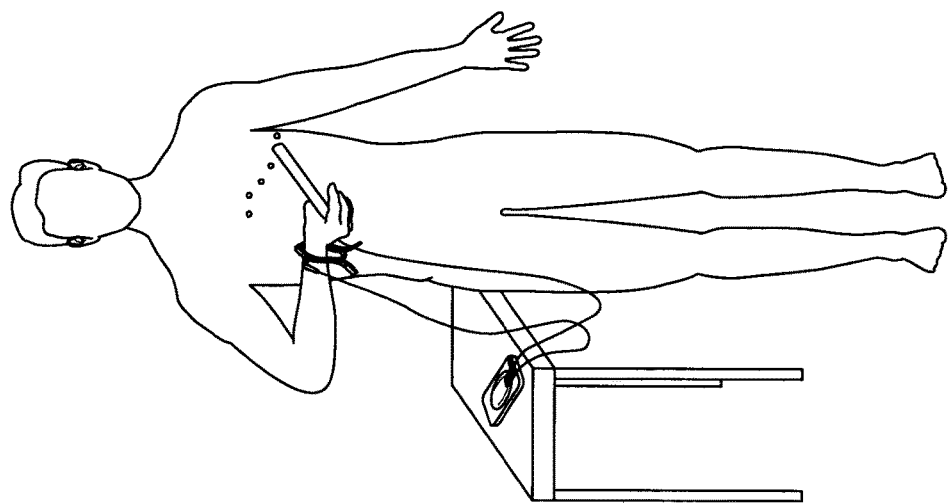
Figure 7E:
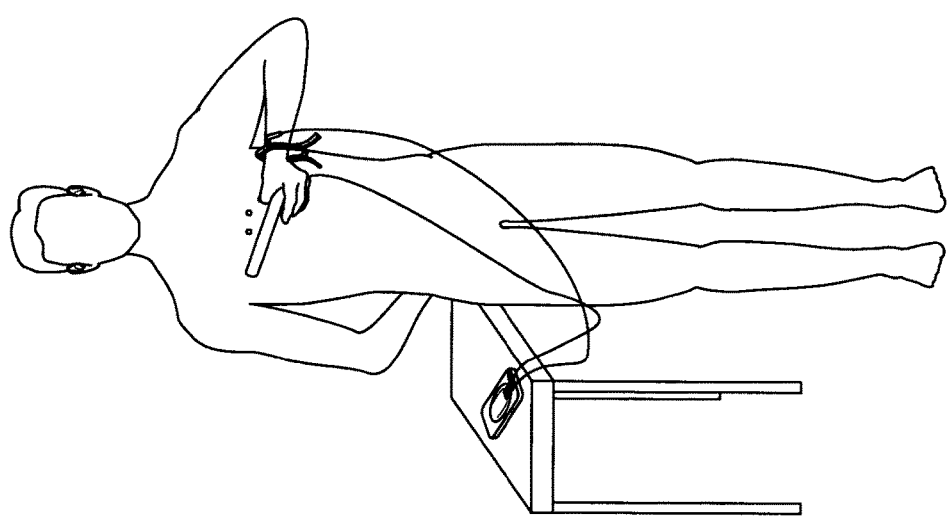

In another embodiment that is shown in FIG. 6 and labeled by way of example with reference numeral 10-1, the electrocardiograph device combines the first and second electrodes 14 and 18 on opposing ends of a unit 50 shaped like a flash light or pen. For example, the electrocardiograph device 10-1 that is shown in FIG. 6 by way of example has a second electrode 18 on a cylindrical surface of one end of the "pen" touching a holder's hand in use. The first electrode 14 is located on an opposing end and is used to contact the holder's chest, hand or other body part when in use. The electrocardiograph device 10-1 can thus be used to measure the electrical signals between the opposing first and second electrodes 14 and 18, respectively.

The devices and apparatuses disclosed herein can also be configured to use one or more disposable first and second electrodes 14 and 18, respectively, or first and second electrode assemblies 12 and 16, respectively. Use of disposable electrodes or disposable electrode assemblies allows the electrocardiograph device 10 or 10-1 to be used by multiple patients with reduced chance spreading disease by transfer of microbes and bodily fluids from one patient to another.

The first and second electrodes 14 and 18, respectively, can be connected to the control circuitry 22 in a wired or wireless manner. In one embodiment, and as shown in FIGS. 5A and 5B, the first and second electrodes 14 and 18, respectively, are electrically connected to the control circuitry 22 by the ports 23-1 and 23-2, and wires or cables.

The control circuitry 22 measures the small voltage between the first and second electrodes 14 and 18, respectively. In one embodiment, the data transmission module 24 converts the voltage measurements to a frequency modulated electrocardiogram audio signal and transmits the signal to a receiver of the computer hardware 34 of the portable computing device 11 via cable, a wired audio jack connection, wirelessly (using, for example, a BLUETOOTH® connection) or acoustically. The receiver of the portable computing device 11 can thus be a cable connection, audio jack, BLUETOOTH® or similar wireless receiver, or a microphone. In order to provide enhanced privacy, in one embodiment, the data transmission module 24 encrypts the signals prior to transmitting to the portable computing device 11. Numerous encryption techniques are known to those skilled in the art.

Nonlimiting examples of portable computing device 11 having, or adaptable to have, such receivers include smartphones, personal digital assistants (PDAs), tablet personal computers, pocket personal computers, notebook computers, desktop computers, and server computers. The receiver may include an antenna and/or a microphone depending upon the types of signals to be transmitted from the data transmission module 24.

In one embodiment, the electrocardiogram signals are converted to a frequency modulated audio or sound signal having a carrier frequency in a range of from about 1 kHz to about 24 kHz or greater and in this case the receiver of the computer hardware 34 will include a microphone. In another embodiment, the data transmission module 24 converts the electrocardiogram signals to a frequency modulated sound signal having a carrier frequency in a range of from about 18 kHz to about 24 kHz or greater. Nonlimiting examples of suitable ultrasonic transmitters include, but are not limited to, miniature speakers, piezoelectric buzzers, and the like. The ultrasonic signals can be received by, for example, a microphone of the computer hardware 34 of the portable computing device 11.

Referring now to FIG. 7, a non-transitory computer readable medium of the computer hardware 34 stores a set of instructions, wherein the set of instructions are capable of being executed by the processor of the portable computing device 11. When the set of instructions are executed, the one or more portable computing device 11 is caused to receive and record electrocardiogram signals between the first electrode 14 and the second electrode 18, while the first and second electrodes 14 and 18, respectively, are sequentially placed in predetermined paired positions on a patient's body at separate and distinct instants of time, and held in each predetermined paired position for multiple heartbeats. The computing device essentially steps the user through the positioning each lead and can, for example, show a picture of a body on a computer screen with the desired electrode positioning indicated by a flashing point. The set of instructions further cause the portable computing device 11 to calculate the electrocardiogram signals into signal sets representing a heartbeat for each paired position, and from the signal sets representing a heartbeat, to calculate average heartbeat representations for each paired position. The set of instructions can then cause the portable computing device 11 to align the average heartbeat representations, and to store and output electrocardiogram data indicative of the average heartbeat representations in a standard 12-lead electrocardiogram format.

For example, ten seconds of each lead can be recorded and an average PQRST computed for each lead from each recording. The limb lead average beats (I, II, and III) can then be time-aligned. Augmented lead average beats are calculated from aligned average limb leads. The V1-V6 beats are averaged and aligned to create a 12-lead report from averaged beats.

The 12-lead electrocardiogram format output can display on the output device 32, such as a display screen of the portable computing device 11 or can be output through a printer. The set of instructions can cause the 12-lead electrocardiogram format output to be retained in a storage memory of the portable computing device 11, or to be transmitted to a computer external to the portable computing device 11, such as a web server via an internet connection on the portable computing device 11.

In one embodiment, the set of instructions can further cause the portable computing device 11 to digitize and demodulate the electrocardiogram signals using technology known to those skilled in the art or technology yet to be developed.

In another embodiment, when the set of instructions are executed, the portable computing device 11 is caused to interact with a user (e.g. via the output device 32) to provide audio and/or textual instructions to direct the placement of the first and second electrodes 14 and 18, respectively, and/or to request the user to confirm placement of the first and second electrodes 14 and 18, respectfully via the input device 30. For example, the portable computing device 11 can be made to provide textual instructions to a user for contacting the first electrode 14 to the patient's left arm and the second electrode 18 to the patient's right arm on a display screen, after which the electrocardiograph device 10 or the electrocardiograph device 10-1 and the portable computing device 11 measures and records the electrical signal between the left arm and right arm for a suitable time interval to correspond to Lead I in a 12-lead ECG. The instructions can further cause the portable computing device 11 to calculate and store an average heartbeat representation for Lead I. A suitable time interval for obtaining heartbeat data for Lead I, and all leads generally, can be between 5 seconds and 30 seconds. Longer times are possible but not necessary.

The set of instructions can further cause the portable computing device 11 to provide instructions to a user, or request placement confirmation from a user, to collect the electrocardiogram data. For example, after the portable computing device 11 has stored the data for Lead I, the portable computing device 11 may provide instructions to the user, or request placement confirmation from the user regarding contacting the first electrode 14 to the patient's left leg and the second electrode 18 to the patient's right arm, wherein the electrical signal measured between the left leg and right arm corresponds to Lead II, and to calculate and store an average heartbeat representation for Lead II.

Similarly, the set of instructions can further cause the portable computing device 11 to provide instructions to a user, or request placement confirmation from a user, regarding contacting the first electrode 14 to the patient's left leg and the second electrode 18 to the patient's left arm, wherein the electrical signal measured between the left leg and the left arm corresponds to Lead III in a 12-lead electrocardiogram and then to analyze the electrical signal corresponding to Lead III to calculate and store an average heartbeat representation for Lead III.

Using the average heartbeat representations Lead I and Lead II, the set of instructions can cause the computing device to calculate aVR, aVL, and aVF. The augmented vector right (aVR) is equal to RA−(LA+LL)/2 or −(I+II)/2. The augmented vector left (aVL) is equal to LA−(RA+LL)/2 or (I−II)/2. The augmented vector foot (aVF) is equal to LL−(RA+LA)/2 or (II−I)/2.

The set of instructions can further cause the portable computing device 11 to provide instructions to a user, or request placement confirmation from the user, for contacting the first electrode 14 with each of the V1, V2, V3, V4, V5, and V6 chest locations while contacting the second electrode 18 to one of the patient's left arm and the patients right arm. The electrical signals measured between each of the V1, V2, V3, V4, V5, and V6 chest locations and the left arm or the right arm correspond to Leads V1, V2, V3, V4, V5, and V6 in a 12-lead electrocardiogram. The set of instructions can then further cause the portable computing device 11 to analyze the electrical signals corresponding to Leads V1, V2, V3, V4, V5, and V6 to calculate average heartbeat representations for Leads V1, V2, V3, V4, V5, and V6.

While not being bound by any particular theory, it has been discovered that use of multiple electrodes to achieve a composite pole such as Wilson's central terminal is not necessary. In one embodiment, the patient's right arm can be used as a negative terminal for each of Leads V1, V2, V3, V4, V5, and V6 captured with conventional placement of electrodes on the chest. In some individuals, however, V1, V2 and V3 measurements do not correlate well. In such individuals, the electrodes must be placed on either side of the heart to achieve duplication of conventional V1, V2 and V3 measurements. It has been definitively demonstrated that in such individuals, the left arm can be used for Leads V1, V2, and V3, while the right arm is used for Leads V4, V5, and V6, and excellent correlation to conventional measurements is achieved.

Once average heartbeat representations are calculated and stored for Leads I, II, III, aVR, aVL, aVF, V1, V2, V3, V4, V5, and V6, the set of instructions can cause the portable computing device 11 to align each of the heartbeat representations based on corresponding characteristics of the heartbeat representations. The averaged and aligned signals can be stored and output in a 12-lead electrocardiogram format.

While it is customary for the voltage measurements to be made in one direction, the software can be made to recognize when the first and second electrodes 14 and 18 are reversed and invert the average heartbeat representation. For example, it is customary for Lead I to measure the left arm (LA) minus the right arm (RA), e.g. I=LA−RA. However, if the first and second electrodes 14 and 18 were reversed such that RA-LA was measured instead, the software would recognize that the first and second electrodes 14 and 18 were reversed and would invert the average heartbeat representation for Lead I to obtain the traditional Lead one output.

Methods for generating a traditional 12-lead electrocardiogram using only two electrodes, e.g. the first and second electrodes 14 and 18, are provided by operating the portable computing device 11 and the above-described electrocardiograph device 10 or 10-1. A 12-lead electrocardiogram can be generated by sequentially measuring electrical signals between the first and second electrodes 14 and 18 at separate and distinct instants of time after the first and second electrodes 14 and 18 are positioned at predetermined locations on a patient's body. Average heartbeat representations for each of the leads can be calculated as described above, and aligned to produce an electrocardiogram having a 12-lead electrocardiogram format.

There are several commonly used 12-lead electrocardiogram formats. The most common format is a 4×3 format; four columns of three leads. The first column includes Limb Leads I, II and III. The second column includes Leads aVR, aVL and aVF. The third column includes Leads V1, V2 and V3, while the fourth column includes Leads V4, V5 and V6.

In some embodiments, the portable computing device 11 is a commercially available smart phone having a standard operating system such as the operating systems identified in the art as "iOS" or "Android." In this embodiment, the electrocardiograph 8 for generating a 12-lead electrocardiogram using only two electrodes can be provided using the above-described electrocardiograph device 10 and software downloadable to the portable computing device 11, wherein the software provides instructions to the portable computing device 11 as described above. In these embodiments, the control circuitry 22 and data transmission module 24 are configured to function and interact with the portable computing device 11 when the portable computing device 11 is executing an application downloadable to the portable computing device 11.

In one embodiment, the systems and methods described above include sending the 12-lead electrocardiogram to a remote server or to a medical professional. In another embodiment, the systems and methods described above include a display and displaying the 12-lead electrocardiogram a on a display screen. Similarly, the systems and methods described above can include a printer and printing the 12-lead electrocardiogram. In yet another embodiment, the methods and systems described above include saving the 12-lead electrocardiogram to a storage memory of the portable computing device 11.

In order to further illustrate the present invention, the following examples are given. However, it is to be understood that the examples are for illustrative purposes only and are not to be construed as limiting the scope of the invention.

EXAMPLE 1

The above-described system was tested on 121 patients in a clinical trial. Each patient was monitored using the conventional 10 electrodes, i.e., placing 6 electrodes on the patient's chest and one electrode on each of the patient's arms and legs. A conventional 12-lead electrocardiogram report was then prepared for each patient using a traditional stationary electrocardiograph sold under the trademark GE® MAC3500.

The electrocardiograph device 10-1 having the first and second electrodes 14 and 18 in a pen-type configuration was tested on each patient and a conventional format 8-lead report was prepared from the sequential measurements. The 2-electrode electrocardiograph calculated the V1-V6 leads using the right hand (RA) for the negative terminal and then the left hand (LA) for the negative terminal. A statistical analysis was made comparing the 2-electrode electrocardiograph results with the traditional 10-electrode electrocardiograph results.

Figure 8:
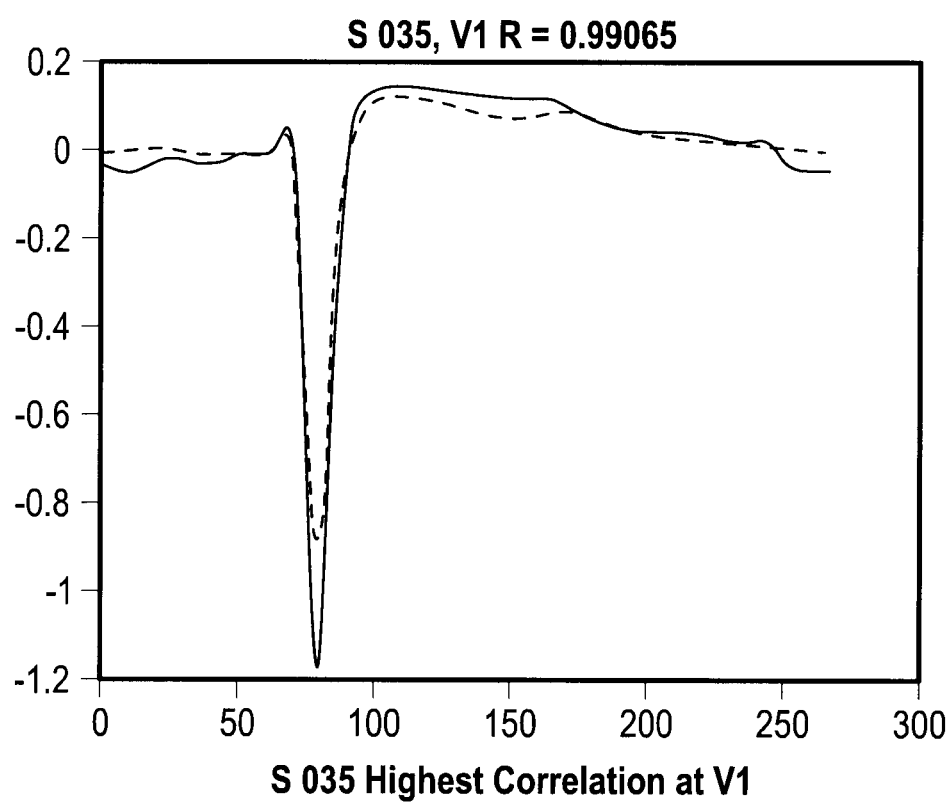
FIG. 8 shows a correlation of V1 leads for Subject 35 of the Example Clinical Trials.

FIG. 8 compares V1 for Subject 35 having the highest correlation between the 10-electrode and the 2-electrode measurements. A correlation coefficient of 0.99 was achieved.

Figure 9:
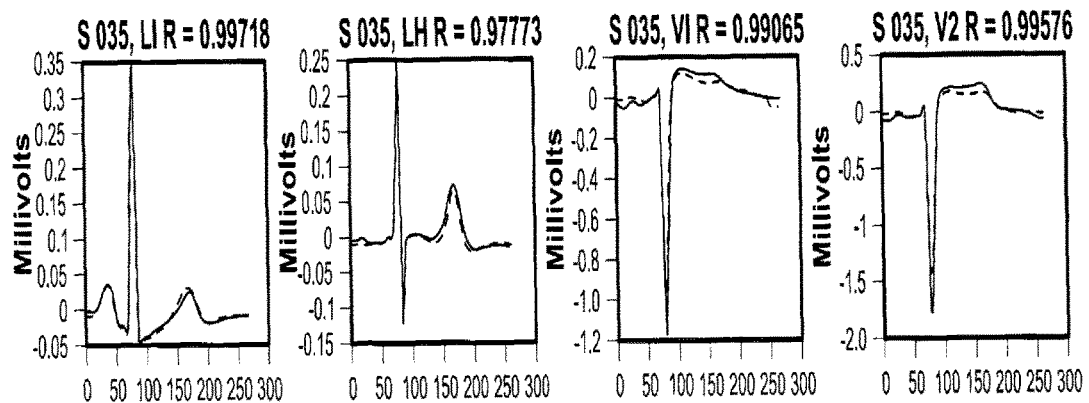
FIG. 9 shows an excellent correlation of leads 1-8 for Subject 35 in the Example Clinical Trials.
Figure 9:
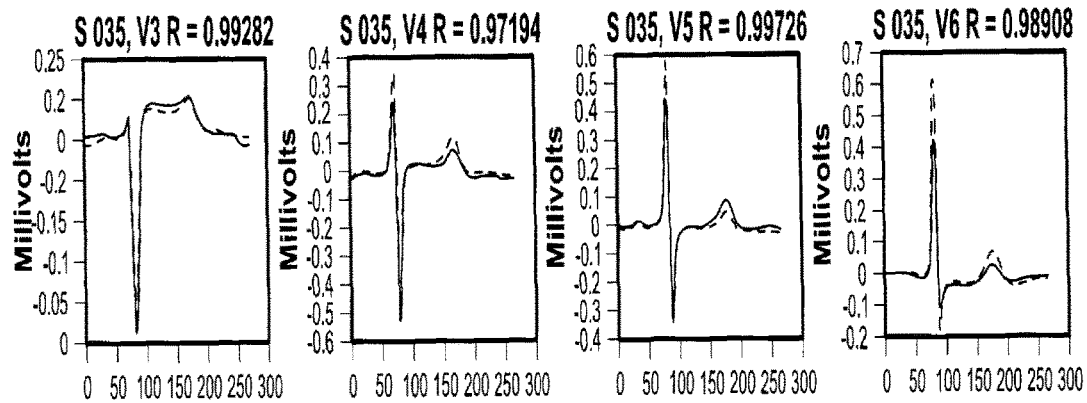

FIG. 9 shows each of the 8 leads for Subject 35, comparing the 10-electrode results with the 2-electrode results. The correlation coefficient averaged over all of the leads was 0.988.

From the above descriptions, it is clear that the presently disclosed and claimed inventive concepts are well-adapted to carry out the objects and to attain the advantages mentioned herein, as well as those inherent in the presently disclosed and claimed inventive concept. While the presented embodiments have been described for purposes of this disclosure, it will be understood that numerous changes may be made which will readily suggest themselves to those skilled in the art and which are accomplished within the spirit of the presently disclosed and claimed inventive concepts.

What is claimed is:

1. An electrocardiograph comprising:
   an electrocardiograph device having (a) a first electrode assembly with a first electrode adapted to measure an electrical signal on a patient's body; (b) a second electrode assembly with a second electrode adapted to measure an electrical signal on the patient's body; (c) control circuitry configured to measure electrocardiogram signals between the first and second electrodes; and (d) a data transmission module configured to transmit the measured electrocardiogram signals to a computing device; and
   a computing device having a non-transitory computer-readable storage medium storing software that includes instructions that when executed by a processor causes the processor to (a) calculate an average PQRST beat from the measured electrocardiogram signals as the first and second electrodes are sequentially placed in Limb Lead I, II, and III positions on a patient's body for a time required to measure at least one heartbeat in each Limb Lead position, the Limb Lead positions known by the processor; (b) use the relationship (Lead III=Lead II−Lead I) to time-align and display Limb Leads I, II, and III; and (c) calculate and display augmented Leads aVR, aVL, and aVF from the time-aligned Limb Leads.

2. The electrocardiograph of claim 1, wherein software further includes instructions that when executed by the processor causes the processor to (d) calculate and display average Leads V1, V2, and V3 from the measured electrocardiogram signals obtained from sequentially placing one of the first and second electrodes in a V1, V2, and V3 position while contacting the other of the first and second electrodes with a left arm of the patient for a time required to measure at least one heart beat; and (e) calculate and display average Leads V4, V5, and V6 from the measured electrocardiogram signals obtained from sequentially placing one of the first and second electrodes in a V4, V5, and V6 position while contacting the other of the first and second electrodes with a right arm of the patient for a time required to measure at least one heartbeat.

3. The electrocardiograph of claim 1 or 2, wherein the data transmission module is configured to transmit the measured electrocardiogram signals to the computing device by wire.

4. The electrocardiograph of claim 1 or 2, wherein the data transmission module is configured to transmit the measured electrocardiogram signals to the computing device wirelessly.

5. The electrocardiograph of claim 1 or 2, wherein at least one of the first and second electrode assemblies comprises a spring-hinged cuff.

6. The electrocardiograph of claim 1 or 2, wherein at least one of the first and second electrode assemblies comprises a disposable electrode.

7. The electrocardiograph device of claim 1 or 2, wherein the portable computing device is a smartphone and the electrocardiograph device further comprises a housing for the control circuitry and the data transmission module, the housing adapted to fit onto or within a protective case for the smartphone.

8. The electrocardiograph device of claim 1 or 2, wherein the data transmission module is further configured to transmit the measured ECG signals as ultrasonic, frequency modulated (FM) sound signals.

9. The electrocardiograph device of claim 1 or 2, wherein the data transmission module is further configured to encrypt and transmit encrypted signals.

10. A non-transitory computer-readable storage medium storing software that includes instructions that when executed by a processor causes the processor to:
receive and record electrocardiogram signals between a first electrode and a second electrode, the first and second electrodes sequentially placed in predetermined paired positions on a patient's body for a time required to measure at least one heartbeat, the paired positions known by the processor and corresponding to Limb Leads I, II and III, and V1, V2, V3, V4, V5, and V6;
for each Limb Lead paired position, determine electrocardiogram signal sets representing a heartbeat and calculate average time-aligned heartbeat representations for Limb Leads I, II and III; and
calculate augmented leads aVR, aVL, and aVF from the average time-aligned heartbeat representations for Limb Leads I, II, and III and output the electrocardiogram signals in a 12-lead electrocardiogram format.

11. The non-transitory computer-readable storage medium of claim 10, wherein the electrocardiogram signals analyzed comprise at least one of wired electrical signals, wireless electromagnetic signals, and acoustic sound signals.

12. The non-transitory computer-readable storage medium of claim 10, wherein the set of instructions, when executed by the processor, further causes the processor to digitize and demodulate frequency modulated electrocardiogram acoustic signals.

13. The non-transitory computer-readable storage medium of claim 10, wherein the set of instructions, when executed by the processor, further causes the processor to interact with a user to identify first and second electrode paired positions corresponding to a lead.

14. The non-transitory computer-readable storage medium of claim 10, wherein the set of instructions, when executed by the processor, further causes the processor to (a) provide instructions to a user or request placement confirmation from the user regarding contacting the first electrode to the patient's left arm and the second electrode to the patient's right arm, wherein the electrical signal measured between the left arm and right arm corresponds to Lead I in a 12-lead electrocardiogram, and (b) analyze the electrical signal corresponding to Lead I to calculate an average heartbeat representation for Lead I.

15. The non-transitory computer-readable storage medium of claim 14, wherein the set of instructions, when executed by the processor, further causes the processor to (c) provide instructions to a user or request placement confirmation from the user regarding contacting the first electrode to the patient's left leg and the second electrode to the patient's right arm, wherein the electrical signal measured between the left leg and right arm corresponds to Lead II in a 12-lead electrocardiogram, and (d) analyze the electrical signal corresponding to Lead II to calculate an average heartbeat representation for Lead II.

16. The non-transitory computer-readable storage medium of claim 15, wherein the set of instructions, when executed by the processor, further causes the processor to (e) provide instructions to a user or request placement confirmation from the user regarding contacting the first electrode to the patient's left leg and the second electrode to the patient's left arm, wherein the electrical signal measured between the left leg and left arm corresponds to Lead III in a 12-lead electrocardiogram, and (f) analyze the electrical signal corresponding to Lead III to calculate an average heartbeat representation for Lead III.

17. The non-transitory computer-readable storage medium of claim 16, wherein the set of instructions, when executed by the processor, further causes the processor to time-align the average heartbeat representations for Lead I and Lead II and calculate aVR, aVL, and aVF average heartbeat representations from the time-aligned average heartbeat representations for Lead I and Lead II.

18. The non-transitory computer-readable storage medium of claim 17, wherein the set of instructions, when executed by the processor, further causes the processor to (g) provide instructions to a user or request placement confirmation from the user regarding contacting the first electrode with each of the V1, V2, V3, V4, V5, and V6 chest locations while contacting the second electrode to one of the patient's left arm and the patients right arm, wherein the electrical signals measured between each of the V1, V2, V3, V4, V5, and V6 chest locations and the left arm or the right arm correspond to Leads V1, V2, V3, V4, V5, and V6 in a 12-lead electrocardiogram, and (h) analyze the electrical signals corresponding to Leads V1, V2, V3, V4, V5, and V6 to calculate average heartbeat representations for Leads V1, V2, V3, V4, V5, and V6.

19. The non-transitory computer-readable storage medium of claim 18, wherein the left arm is used for Leads V1, V2, and V3 and the right arm is used for Leads V4, V5, and V6.

20. The non-transitory computer-readable storage medium of claim 18, wherein the right arm is used for each of Leads V1, V2, V3, V4, V5, and V6.

21. The non-transitory computer-readable storage medium of claim 18, wherein the set of instructions, when executed by the processor, further causes the processor to (i) output the average heartbeat representations for Leads I, II, III, aVR, aVL, aVF, V1, V2, V3, V4, V5, and V6.

22. A method for generating a 12-lead electrocardiogram using an electrocardiograph comprising an electrocardiograph device and a portable computing device, the method comprising:
operating a portable computing device and an ECG device having a first electrode, a second electrode, control circuitry, and a data transmission module, the control circuitry configured to measure ECG signals between the first and second electrodes, the data transmission module configured to transmit the measured ECG signals to the portable computing device;
sequentially measuring ECG signals between the first and second electrodes positioned at predetermined locations on a patient's body; and
using the portable computing device to generate a 12-lead ECG from the sequentially measured ECG signals between the first and second electrodes.

23. The method of claim 22, wherein the step of sequentially measuring ECG signals comprises:
contacting one of the first and second electrodes with a left arm of a patient while contacting the other of the first and second electrodes with a right arm of the patient to measure an electrical signal corresponding to a Lead I;
contacting one of the first and second electrodes with a left leg of the patient while contacting the other of the first and second electrodes with the right arm of the patient to measure an electrical signal corresponding to a Lead II;
contacting one of the first and second electrodes with the left leg of the patient while contacting the other of the first and second electrodes with the left arm of the patient to measure an electrical signal corresponding to a Lead III;
sequentially contacting one of the first and second electrodes with a V1, V2, V3, V4, V5, and V6 chest location on the patient while contacting the other of the first and second electrodes with the patient's left arm or the patient's right arm to measure electrical signals corresponding to a Leads V1, V2, V3, V4, V5, and V6, respectively.

24. The method of claim 22, wherein the step of sequentially measuring ECG signals comprises:
contacting one the first and second electrodes with a left arm of a patient while contacting the other of the first and second electrodes with a right arm of the patient to measure an electrical signal corresponding to a Lead I;
contacting one of the first and second electrodes with a left leg of the patient while contacting the other of the first and second electrodes with the right arm of the patient to measure an electrical signal corresponding to a Lead II;
contacting one of the first and second electrodes with the left leg of the patient while contacting the other of the first and second electrodes with the left arm of the patient to measure an electrical signal corresponding to a Lead III;
sequentially contacting one of the first and second electrodes with a V1, V2, and V3 chest location on the patient while contacting the other of the first and second electrodes with the left arm of the patient to measure electrical signals corresponding to Leads V1, V2, and V3, respectively; and
sequentially contacting one of the first and second electrodes with a V4, V5 and V6 chest location on the patient while contacting the other of the first and second electrodes with the right arm of the patient to measure electrical signals corresponding to Leads V4, V5, and V6, respectively.

25. The method of claim 24, further comprising using the portable computing device to time-align the average heartbeat representations for Lead I and Lead II, and calculate aVR, aVL, and aVF from the time-aligned average heartbeat representations for Lead I and Lead II.

26. The method of claim 25, further comprising using the portable computing device to output the ECG signals in a 12-lead ECG format.

27. A system for generating a 12-lead ECG using two electrodes comprising:
a first electrode assembly having a first electrode adapted to measure an electrical signal on a patient's body;
a second electrode assembly configured to removably attach to an upper limb of the patient, the second electrode assembly having a second electrode adapted to measure an electrical signal on the patient's body;
control circuitry configured to measure ECG signals between the first and second electrodes;
a data transmission module configured to transmit the measured ECG signals to a portable computing device; and
a non-transitory computer-readable storage medium storing a set of instructions capable of being executed by one or more computing devices, that when executed by the one or more computing devices causes the one or more computing devices to: (a) analyze ECG signals between a first electrode and a second electrode, the first and second electrodes sequentially placed in predetermined paired positions on a patient's body; (b) average the ECG signals for each paired position to calculate average heartbeat representations for each paired position; and (c) time-align the average heartbeat representations to output in a 12-lead ECG format.

28. The system of claim 27, wherein the first electrode assembly is configured to be hand held.

29. The system of claim 27, wherein the second electrode assembly comprises a spring-hinged cuff.

30. The system of claim 27, wherein the set of instructions, when executed by the one or more computing devices, further causes the one or more computing devices to interact with a user to identify first and second electrode paired positions corresponding to a lead.

31. The system of claim 27, wherein the set of instructions, when executed by the one or more computing devices, further causes the one or more computing devices to (a) provide instructions to a user or request placement confirmation from the user regarding contacting the first electrode to the patient's left arm and the second electrode to the patient's right arm, wherein the electrical signal measured between the left arm and right arm corresponds to Lead I in a 12-lead ECG, and (b) analyze the electrical signal corresponding to Lead I to calculate an average heartbeat representation for Lead I.

32. The system of claim 31, wherein the set of instructions, when executed by the one or more computing devices, further causes the one or more computing devices to (c) provide instructions to a user or request placement confirmation from the user regarding contacting the first electrode to the patient's left leg and the second electrode to the patient's right arm, wherein the electrical signal measured between the left arm and right arm corresponds to Lead II in a 12-lead ECG, and (d) analyze the electrical signal corresponding to Lead II to calculate an average heartbeat representation for Lead II.

33. The system of claim 32, wherein the set of instructions, when executed by the one or more computing devices, further causes the one or more computing devices to (e) provide instructions to a user or request placement confirmation from the user regarding contacting the first electrode to the patient's left leg and the second electrode to the patient's left arm, wherein the electrical signal measured between the left arm and right arm corresponds to Lead III in a 12-lead ECG, and (f) analyze the electrical signal corresponding to Lead III to calculate an average heartbeat representation for Lead III.

34. The system of claim 33, wherein the set of instructions, when executed by the one or more computing devices, further causes the one or more computing devices to timealign the average heartbeat representations for Lead I and Lead II and calculate aVR, aVL, and aVF from the time-aligned average heartbeat representations for Lead I and Lead II.

35. The system of claim 34, wherein the set of instructions, when executed by the one or more computing devices, further causes the one or more computing devices to (g) provide instructions to a user or request placement confirmation from the user regarding contacting the first electrode with each of the V1, V2, V3, V4, V5, and V6 chest locations while contacting the second electrode to one of the patient's left arm and the patients right arm, wherein the electrical signals measured between each of the V1, V2, V3, V4, V5, and V6 chest locations and the left arm or the right arm correspond to Leads V1, V2, V3, V4, V5, and V6 in a 12-lead ECG, and (h) analyze the electrical signals corresponding to Leads V1, V2, V3, V4, V5, and V6 to calculate average heartbeat representations for Leads V1, V2, V3, V4, V5, and V6.

36. The system of claim 35, wherein the left arm is used for Leads V1, V2, and V3 and the right arm is used for Leads V4, V5, and V6.

* * * * *